United States Patent [19]

Hughes

[11] Patent Number: 5,745,545
[45] Date of Patent: Apr. 28, 1998

[54] ALIGNMENT SYSTEM AND METHOD FOR INTRA-OPERATIVE RADIATION THERAPY

[75] Inventor: John H. Hughes, Martinez, Calif.

[73] Assignee: Siemens Medical Systems, Inc., Iselin, N.J.

[21] Appl. No.: 708,066

[22] Filed: Aug. 16, 1996

[51] Int. Cl.⁶ .................................................. G21K 5/16
[52] U.S. Cl. ............................ 378/65; 378/68; 378/206
[58] Field of Search .............................. 378/65, 64, 68, 378/69, 205, 206

[56] References Cited

U.S. PATENT DOCUMENTS

| | | | |
|---|---|---|---|
| 4,314,158 | 2/1982 | Lucido | 250/505 |
| 4,638,814 | 1/1987 | Spanswick | 138/804 |
| 5,027,818 | 7/1991 | Bova et al. | 378/65 X |
| 5,233,990 | 8/1993 | Barnes | 378/65 X |
| 5,315,630 | 5/1994 | Sturm et al. | 378/68 X |
| 5,446,548 | 8/1995 | Gerig et al. | 356/375 |
| 5,553,112 | 9/1996 | Hardy et al. | 378/65 X |

*Primary Examiner*—David P. Porta

[57] ABSTRACT

A system and method for applying radiation therapy include utilizing a radiation applicator that is spaced apart from and mechanically independent of a radiation source. An array of targets is affixed to the radiation applicator and cameras image the targets to determine coordinates that are compared to desired target coordinates. If there is a correlation between actual target coordinates and desired coordinates, radiation source-to-applicator alignment is achieved. Consequently, the patient is properly positioned relative to a radiation beam, such as an electron beam. On the other hand, if the actual and desired coordinates are different, the relative position of the radiation source and the gantry is adjusted. Preferably, the adjustment is automated.

19 Claims, 4 Drawing Sheets

ALIGNMENT SYSTEM AND METHOD FOR INTRA-OPERATIVE RADIATION THERAPY

BACKGROUND OF THE INVENTION

The invention relates generally to aligning elements for applying radiation to a patient and more particularly to systems and methods for properly aligning a source of radiation with an applicator for intra-operative radiation therapy.

DESCRIPTION OF THE RELATED ART

Radiation-emitting devices are generally known and used, for instance, as radiation therapy devices for the treatment of patients. A radiation therapy device typically includes a gantry which can be swiveled about a horizontal axis of rotation in the course of a therapeutic session. A linear accelerator is located in the gantry for generating a high-energy radiation beam. The high-radiation beam can be electron radiation or photon (X-ray) radiation. During treatment, the radiation beam is trained on a treatment site of a patient lying in the isocenter of the gantry rotation. Typically, the patient is supported on a rotatable table. The combination of movements of the gantry and the table permits movement of the patient about mutually perpendicular X, Y and Z axes. These rotations are sometimes referred to by the terms "tilt," "roll" and "yaw," respectively.

Prior to the application of radiation, a treatment setup process is followed. This process includes setting beam parameters such as radiation energy, field size, exposure times, dose and distance. Moreover, the process includes aligning the gantry, a collimator and the patient. The radiation beam is directed at diseased material, but with a goal of minimizing any adverse effect upon adjacent healthy tissue.

For intra-operative treatments, the alignment process also includes aligning an applicator relative to the patient and the source of radiation. Intra-operative treatment typically includes forming an incision through which an electron beam is directed to a treatment site. The applicator is both mechanically and electrically isolated from the source, i.e. the gantry. Mechanical independence is desirable, since the mass of the gantry operates against the ability to manipulate the radiation beam to enter a relatively small operative incision without significant risk to the patient. The applicator is fixed relative to the patient, typically by attachment to the table. The applicator provides beam collimation close to the patient by establishing a radiation field-defining aperture. Thus, the mechanical isolation reliably limits exposure to the desired treatment site.

Electrical isolation is a factor, since any leakage currents from the gantry to the patient place the patient at risk. U.S. Pat. No. 4,638,814 to Spanswick, which is assigned to the assignee of the present invention, asserts that a patient cannot be subjected to ground leakage currents which exceed five micro amperes because blood and body fluids are good electrolytes and because any electrical devices that are in contact with the patient may be disturbed. Spanswick describes a method of aligning an electron applicator with an electron beam source. A number of laser units project beams of light toward a support ring of the electron applicator. The beams are arranged in a mutual orientation, such as four laser units arranged at 90° intervals. Each of the four laser units includes a beam splitter, so that eight beams are formed. The eight beams form four beam pairs, with the two beams of a pair overlapping at a predetermined point from the electron beam source. Consequently, when the support ring is along the plane through the points of intersection, the eight beams form only four areas of illumination. The electron applicator is attached to the operating table, so that the operating table is moved until there are only the four illuminated regions. In addition to aligning the electron applicator and the electron beam source, the use of the intersecting beams determines the spacing between the applicator and the source.

While the system described in Spanswick provided an improvement over the prior art, further improvements are available. Since the positioning of the electron applicator based upon overlapping beams is performed visually, the process is subject to human error. Moreover, the patent points out that the beams must be "exceedingly sharp" in order to achieve precise positioning. As a result, the accuracy of the method depends upon the selection of the sources of the light beams. Another concern relates to the ability to change the spacing between the electron applicator and the electron beam source. This spacing will partially determine the intensity of the electron beam at the treatment site of the patient. If the intersection of beams is to be used to determine the spacing between the electron applicator and the electron beam source, the light beam axes must be adjusted from session to session when the electron beam intensities vary among sessions. This increases the setup time for equipment which is in demand.

What is needed is a system and method for accurately and efficiently positioning a beam applicator without requiring the beam applicator to be connected to a source of the beam.

SUMMARY OF THE INVENTION

A system for applying radiation therapy includes a radiation source that emits a radiation beam into an applicator that is spaced apart from and mechanically independent of the radiation source. An array of targets is affixed to the applicator and at least one imaging device is affixed to the radiation source to form image data representative of the targets. The image data is processed to determine the positions of the targets. In one embodiment, the determination of the target positions is used to automatically adjust either the applicator positioning or the radiation source positioning until the target positions match predefined coordinates. Preferably, the target positioning is determined in three dimensions.

A method of applying the therapeutic radiation includes attaching the applicator so that it has an orientation that is substantially fixed relative to a patient. The applicator is imaged by the imaging devices that are affixed to the radiation source. Based upon the image data, the system determines whether a desired source-to-applicator alignment has been achieved. The relative positioning of the radiation source and the applicator is adjusted until the desired source-to-applicator alignment is achieved. A radiation beam is then directed into the applicator for applying localized radiation to a treatment site. In the preferred embodiment, the method is used for intra-operative radiation therapy.

DETAILED DESCRIPTION

Figure 1:
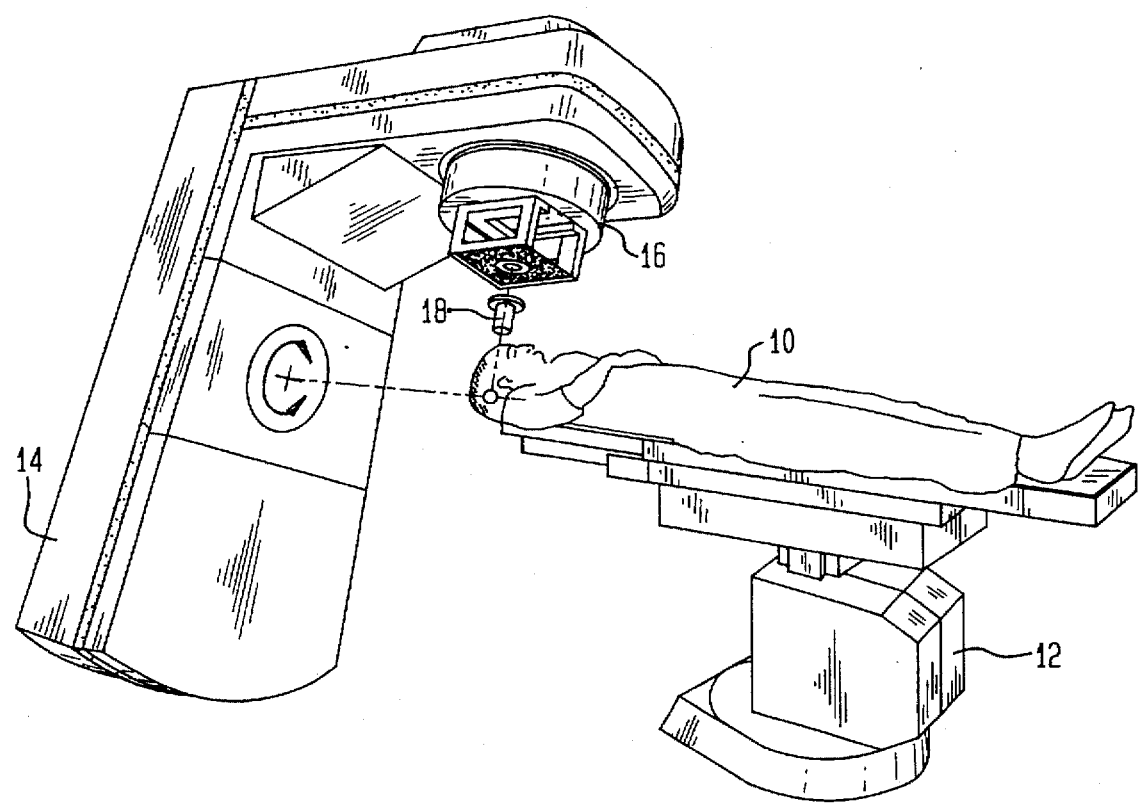
FIG. 1 is a schematical view of a system for applying localized radiation for intra-operative radiation therapy in accordance with the prior art.

With reference to FIG. 1, a patient 10 is shown as resting on a table 12 under a gantry 14 of a radiation therapy machine. A radiation beam is directed from a collimator 16 of the gantry toward the patient. The radiation beam is generated by a linear accelerator within the gantry and is emitted from the collimator. The radiation beam may be electron radiation or photon radiation, i.e. X-ray radiation. The gantry is known in the art.

Typically, the collimator 16 determines the final beam geometry. The beam is directed at a treatment site, such as diseased brain tissue of the patient 10. The table 12 and the gantry 14 are maneuvered to provide the desired alignment of the patient 10 to the radiation beam, and the beam is then generated. However, there are circumstances in which it is undesirable to use the collimator 16 as the component for final direction of the radiation beam at the patient. For example, within an intra-operative treatment an incision is formed for passage of an electron beam to a treatment site. An electron beam tends to expand more quickly than an X-ray beam, so that there is greater concern that healthy tissue will be exposed. To reduce the risk, a radiation applicator 18 is utilized. The radiation applicator is spaced apart from the collimator 16 and may have an output end inserted into the incision of the patient 10. The radiation applicator is formed of a material that is opaque to the electron beam, but includes a passageway to the treatment site. The radiation applicator localizes the therapy to the desired treatment site.

Figure 2:
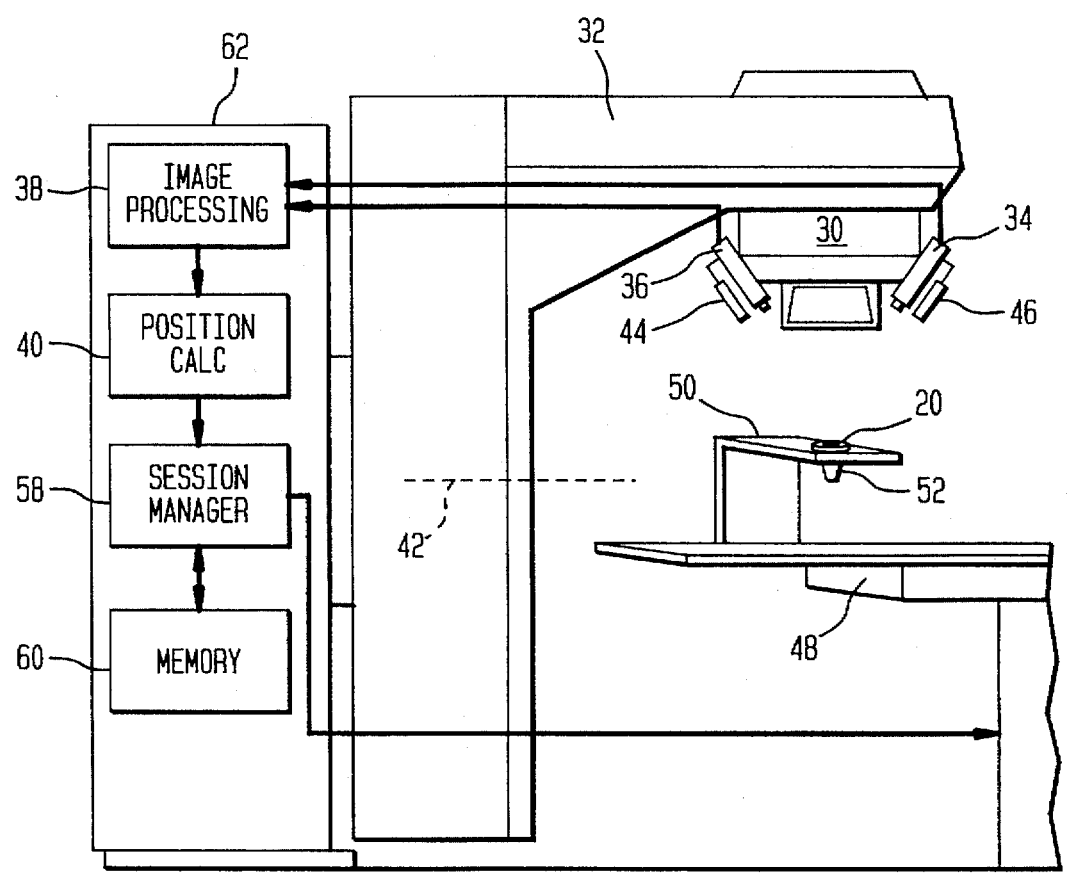
FIG. 2 is a schematical view of a system of applying localized radiation in accordance with the invention.
Figure 3:
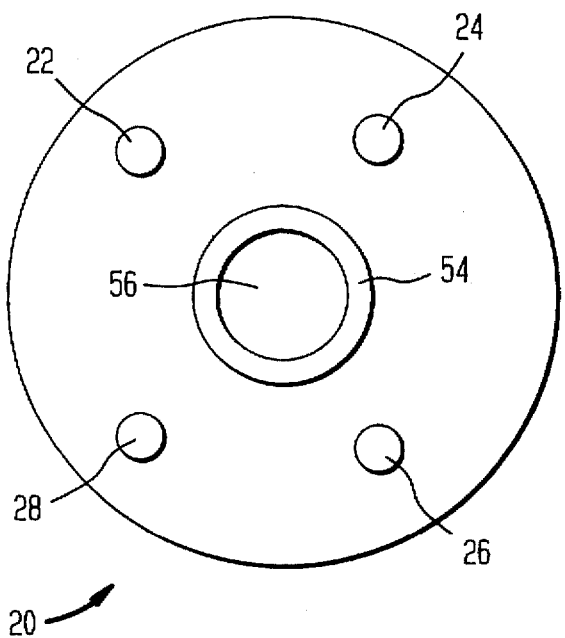
FIG. 3 is a top view of a radiation applicator having targets in accordance with the invention.

Referring now to FIGS. 2 and 3, a radiation applicator 20 in accordance with the preferred embodiment of the invention is shown as including four targets 22, 24, 26 and 28. The targets may be recesses within the surface of the applicator, but preferably are separate members that are formed of a material that facilitates imaging of the targets. As will be explained more fully below, the targets are imaged in order to calculate the spacing and the alignment of the radiation applicator relative to a collimator 30 of the gantry 32 shown in FIG. 2.

While not critical, the targets 22, 24, 26 and 28 are preferably fabricated in the manner described in U.S. Pat. No. 5,446,548 to Gerig et al., which is assigned to the assignee of the present invention. The Gerig et al. patent describes a patient positioning and monitoring system that can be utilized in combination with the invention to be described below.

The targets 22, 24, 26 and 28 preferably include retroreflective material. The arrangement of the targets on the surface of the applicator 20 is not critical. The targets are imaged by a pair of cameras 34 and 36. The cameras may be charge coupled device (CCD) cameras, but other imaging devices may be utilized. The image signals from the cameras 34 and 36 are input to an image processing circuit 38. The image processing circuit cooperates with a position calculation circuit 40 to determine position data for the radiation applicator 20. The image and position processing may include a visual-based coordinate measurement (VCM) system to determine target positioning in three-dimensional space. In the preferred embodiment, the VCM system is a software package which can be integrated with commercially available solid-state cameras, image acquisition and processing boards, and computer hardware. The VCM system combines principles of stereo vision, photogrammetry and knowledge-based techniques to provide precise coordinate and dimension measurement of objects. The two cameras 34 and 36 and the three-dimensional image and position processing of circuits 38 and 40 are calibrated such that the frame of reference is coincident with the system, with an isocenter defined as 0,0,0. The coordinate system is defined such that the X axis lies on a horizontal plane perpendicular to a gantry axis 42 of rotation and passes through the system isocenter, the Y axis is parallel to the gantry axis of rotation and passes through the isocenter, and the Z axis is mutually perpendicular to the other two axes and defines patient height.

Light sources 44 and 46 may be used to enhance performance of the target imaging. In the preferred embodiment, the light sources provide infrared radiation, and each of the cameras 34 and 36 includes an infrared filter. The infrared radiation enables the system to more reliably distinguish light reflected from the targets 22–28, as opposed to background radiation that may be present in the therapy room under ambient light conditions. The light sources may be infrared lasers, with the infrared radiation being spread by lenses, not shown. The use of laser light sources provides the advantage that the spectral bandwidth of the radiation is narrow, providing a further reduction in background interference. Equipping the cameras 34 and 36 with infrared filters reduces the susceptibility of the cameras to background radiation.

The radiation applicator 20 of FIGS. 2 and 3 is shown as being attached to a displaceable table 48 by an L-shaped support device 50. The mechanism for suspending the radiation applicator is not critical. In fact, the applicator may be fixed to the patient, rather than to the table 48. For example, headgear may be fitted to the patient to attach the radiation applicator to the patient.

The radiation applicator 20 is shown as having a truncated cone-shaped beam outlet end 52. The configuration of the inlet and outlet ends of the applicator will depend upon the gantry 32 and the treatment plan of the patient. In the view of FIG. 3, the sloping interior surface 54 is shown as terminating in a circular outlet 56. However, other geometries are contemplated.

The determination of the positions of the targets 22–28 by the image and position processing circuitry 38 and 40 is input to a session manager 58. Based upon inputted data and/or stored data in memory 60, the session manager controls the variable components of the system. In the preferred embodiment, the session managing is completely automated. However, manual adjustments may be required. The session manager 58 may therefore include an operator console and input devices, such as a keyboard.

The session manager 58 compares the positions of the targets 22–28 to preselected coordinates. If the positions of the targets are different than the desired positions, either or both of the gantry 32 and the table 48 are manipulated to reposition the targets. The session manager is housed within a stationary portion 62 of the system that supports the rotatable portion of the gantry 32. The rotatable portion rotates about the gantry axis 42. The table 48 accommodates repositioning along the X axis and the Z axis. Preferably, the circuitry within the stationary portion 62 of the system utilizes a servo approach, so that periodic image captures via the cameras 34 and 36 are utilized to establish the desired target coordinates. Since the table 48 supports the patient, repositioning the radiation applicator 20 relative to the gantry 32 also repositions the patient. As a consequence, manipulation of the gantry 32 or the table 48 does not affect the position of the applicator 20 relative to the patient.

Figure 4:
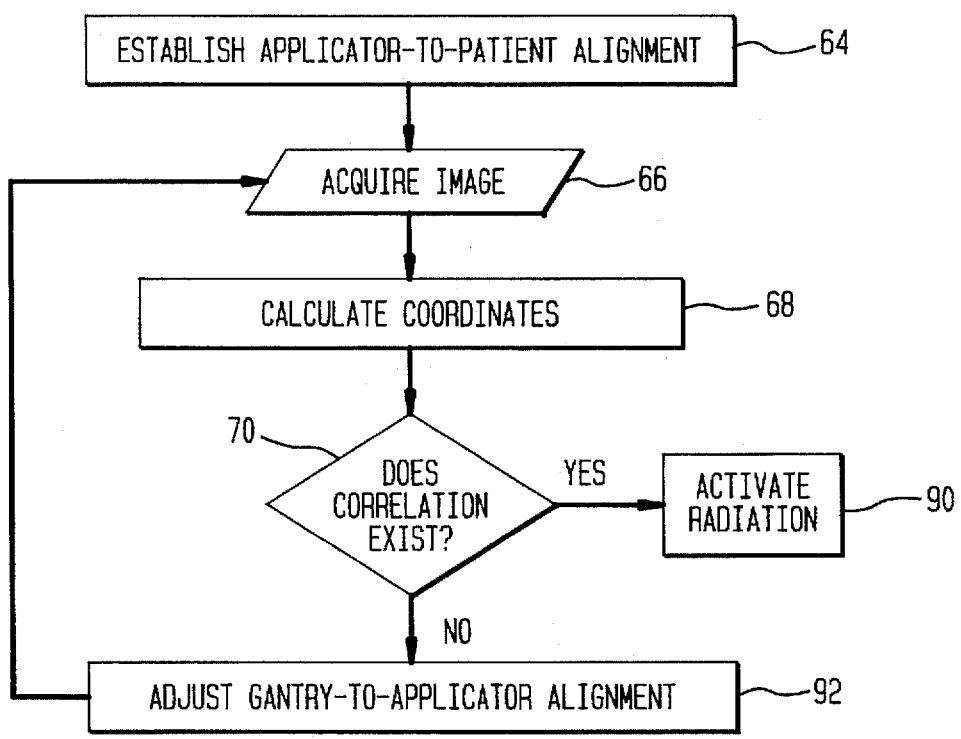
FIG. 4 is a process flow view of a method for utilizing the system of FIG. 2.

The operation of the system of FIG. 2 is described with reference to FIGS. 2–4. In step 64, the alignment of the applicator 20 to the patient is established. In one embodiment, the applicator-support device 50 is attached to the table 48. While not shown, the device 50 preferably includes an adjustment mechanism. For example, the device may include slide mechanisms that permit vertical and horizontal repositioning of the applicator 20. In another embodiment, the applicator 20 is supported directly by the patient.

The applicator is secured to provide the desired angular alignment relative to a treatment site of the patient. This reduces the risk that healthy tissue will be unnecessarily exposed to radiation. The alignment of the applicator also includes setting the distance between the treatment site and the beam outlet end 52 of the applicator 20.

At step 66, the cameras 34 and 36 of FIG. 2 acquire an image of the targets 22–28. Each camera detects the reflected radiation from the targets. As previously noted, the preferred embodiment includes infrared lasers 44 and 46 and infrared filters in order to reduce the effects of background radiation on the image processing at circuit 38.

At least two cameras 34 and 36 are employed in order to permit position calculation 68 in three dimensions. Stereo vision techniques of a video-based coordinate measurement system are executed within the position calculation circuit 40 to determine coordinates within a coordinate system defined such that the X axis lies in a horizontal plane perpendicular to the gantry axis 42, the Y axis is parallel to the gantry axis, and the Z axis is perpendicular to the other two axes and defines patient height. Each of the three axes of the coordinate system passes through the isocenter of the radiation system.

Figure 5:
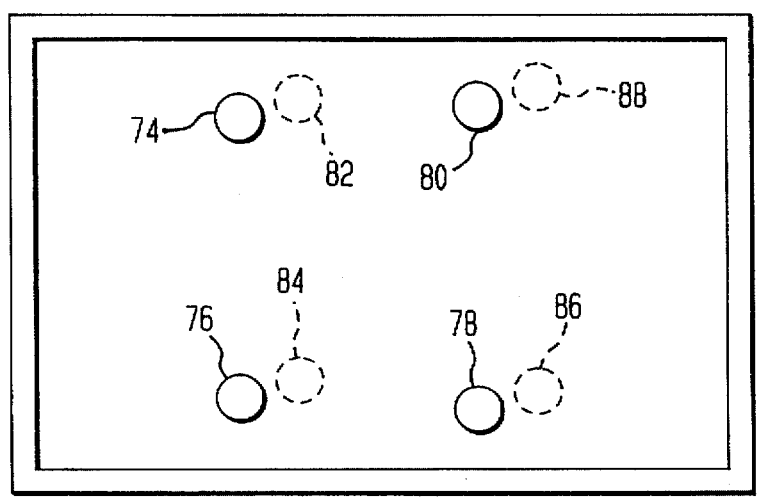
FIG. 5 is a front view of a display screen for the applicator of FIG. 3.

In step 70, a determination is made as to whether the calculated coordinates of the targets 22–28 match desired coordinates. The position data related to the desired coordinates may be stored in memory 60 of FIG. 2. The determination of whether a correlation exists preferably takes place in software. However, referring briefly to FIG. 5, the determination may be made by an operator using a display 72 that shows both the desired positions 74, 76, 78 and 80 of the targets and the actual positions 82, 84, 86 and 88. If the desired positions and the actual positions are aligned, the applicator 20 is properly aligned with the gantry 32. Consequently, the treatment site of the patient is properly aligned with the radiation beam that will be emitted from the gantry. In such case, the source of radiation can be activated, as shown at step 90 in FIG. 4. If at step 70 no correlation is determined between the coordinates calculated in step 68 and the desired target coordinates, the gantry-to applicator alignment is adjusted at step 92. The realignment may be executed in alternative manners. The stationary portion 62 of the gantry 32 may rotate the displaceable portion about gantry axis 42. Alternatively, the table may be manipulated to correct for tilt and roll. The collimator 30 of the gantry 32 is also adjustable, as is well known in the art. Of course, the gantry-to-applicator alignment may be a combination of these adjustments.

Following the realignment at step 92, the process returns to step 66 in order to acquire an updated image for calculation of updated position data in step 68. Preferably, the steps 66, 68, 70 and 92 utilize servo techniques to automatically and efficiently obtain the desired gantry-to-applicator alignment. When the alignment is achieved, the radiation therapy is initiated at step 90. The arrangement of targets 22–28 is not critical. Preferably, there are three or four targets, but performance may be enhanced in some applications by providing a different number. As previously noted, the targets may be merely recessed or raised areas of the applicator servo, but retroreflective targets enhance the image processing by reducing the effect of background radiation. Fluorescent and phosphorescent materials may also be utilized with the appropriate camera filters to enhance selectivity of reception.

In another embodiment, the targets 22–28 are fixed within the sloping interior surface 54 of the applicator 20 of FIG. 3. This allows the targets to be at different distances from the collimator 30 of FIG. 2, even when the applicator is in the desired position relative to the collimator. The variations in distance facilitate distinguishing actual positions of targets from desired target positions.

I claim:

1. A system for applying radiation therapy comprising:
   a radiation source for emitting a radiation beam having a beam axis;
   an applicator spaced apart from said radiation source, said applicator being mechanically independent of said radiation source, said applicator having a beam inlet end and a beam outlet end;
   a plurality of targets affixed to said applicator in a single configuration which enables said applicator to be used on a plurality of patients;
   imaging means affixed to said radiation source for forming image data representative of said targets; and
   position means for determining positions of said targets based upon said image data.

2. The system of claim 1 wherein said imaging means includes a plurality of cameras directed at said applicator.

3. The system of claim 1 further comprising automated means for adjusting an alignment of said beam axis and said applicator based upon positions of said targets as determined by said position means.

4. The system of claim 1 wherein said position means has an output indicative of said positions of said targets in three dimensions.

5. The system of claim 1 further comprising a patient table for supporting a medical patient, said applicator being fixed to said patient table.

6. The system of claim 5 wherein said radiation source and said patient table are independently displaceable.

7. The system of claim 1 further comprising a laser light source directed to illuminate said targets.

8. The system of claim 7 wherein said targets have retroreflective material exposed to said laser light source.

9. The system of claim 1 further comprising memory means for storing desired positions of said targets relative to said imaging means, said system further comprising means for comparing said stored desired positions to said target positions determined by said position means.

10. A method of localizing radiation for application to a plurality of patients comprising steps of:
    (a) providing an applicator having an array of fixed-position targets;
    (b) attaching an applicator such that said applicator has an orientation that is substantially fixed relative to a patient;
    (c) supporting a radiation source adjacent to said applicator;
    (d) imaging said targets on said applicator to determine a first alignment of said radiation source and said applicator;

(e) determining whether said first alignment is a desired source-to-applicator alignment for applying radiation to said patient;

(f) if said first alignment does not match said desired source-to-applicator alignment, adjusting the relative positioning of said radiation source and applicator and repeating steps (d) and (e);

(g) when said desired source-to-applicator alignment is achieved, executing a therapy session that includes generating a radiation beam to enter said applicator;

(h) repeating steps (b) through (g) for a different patient utilizing said applicator.

11. The method of claim 10 further comprising a step of determining positions of said targets in three dimensions.

12. The method of claim 10 wherein said step (b) of attaching said applicator is a step of fixing said applicator to direct radiation through an incision in said patient.

13. The method of claim 10 wherein said step (f) of adjusting said relative positioning includes at least one of repositioning a gantry and repositioning a patient table on which said patient is supported.

14. The method of claim 13 wherein step (f) is an automated step of repositioning at least one of said gantry and said patient table.

15. A system for applying localized therapeutic radiation comprising:

a displaceable gantry having a collimator for directing a radiation beam along a beam axis;

a displaceable patient table mechanically independent of said gantry for supporting a patient to receive radiation therapy;

an applicator supported by said patient table for directing said radiation beam to said patient, said applicator having targets attached to said applicator in fixed positions for use with a plurality of patients;

imaging means supported by said gantry for forming image signals indicative of said targets;

means for determining positions of said targets in three dimensions based upon said image signals;

memory having stored position data indicative of predetermined desired positions of said targets for radiation therapy sessions of a plurality of patients; and means, responsive to selection of a particular patient from said plurality of patients, and responsive to said means for determining said positions of said targets, for aligning said radiation beam and said applicator based upon stored position data specific to said particular patient.

16. The system of claim 15 further comprising means for automatically varying at least one of said gantry and said patient table.

17. The system of claim 15 wherein said targets include retroreflective material.

18. The system of claim 15 wherein said imaging means includes a plurality of cameras and light sources.

19. The system of claim 18 wherein said imaging means further includes an infrared filter for each camera, said light sources being infrared lasers.

* * * * *

UNITED STATES PATENT AND TRADEMARK OFFICE
CERTIFICATE OF CORRECTION

PATENT NO. : 5,745,545
DATED : April 28, 1998
INVENTOR(S) : John H. Hughes

It is certified that error appears in the above-identified patent and that said Letters Patent is hereby corrected as shown below:

On the title page, item [56] please add.

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 4 | 6 | 6 | 2 | 2 | 1 | 2 | 06/09/87 | Brahme | | | |
| | | | | | | | | | | | | | |

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | GB | 22 | 11 | 7y | 0 | 9 | A | 05/07/89 | United Kingdom | | | | |
| | | EP | 0 | 1 | 83 | 9 | 2 | 4 | 11/06/86 | Europe | | | | |
| | | | | | | | | | | | | | | |

Signed and Sealed this

Fourth Day of May, 1999

*Attest:*

*Attesting Officer*

Q. TODD DICKINSON

*Acting Commissioner of Patents and Trademarks*